US011776284B2

(12) United States Patent
Jalenques (10) Patent No.: US 11,776,284 B2
(45) Date of Patent: *Oct. 3, 2023

(54) PROCESS AND DEVICE FOR COLONY COUNTING (71) Applicant: Interscience, St Nom la Breteche (FR)

(72) Inventor: Emmanuel Jalenques, St Nom la Breteche (FR)

(73) Assignee: INTERSCIENCE, St Nom la Breteche (FR)

( * ) Notice: Subject to any disclaimer, the term of this patent is extended or adjusted under 35 U.S.C. 154(b) by 352 days.

This patent is subject to a terminal disclaimer.

(21) Appl. No.: 16/951,185

(22) Filed: Nov. 18, 2020

(65) Prior Publication Data

US 2021/0081647 A1    Mar. 18, 2021

Related U.S. Application Data (62) Division of application No. 15/877,636, filed on Jan. 23, 2018, now Pat. No. 10,872,226.

(30) Foreign Application Priority Data

Jan. 23, 2017 (FR) ..................... 17 50530

(51) Int. Cl.
C12M 3/00 (2006.01)
B01L 3/00 (2006.01)
(Continued)

(52) U.S. Cl.
CPC ........... *G06V 20/693* (2022.01); *C12M 41/36* (2013.01); *C12Q 1/04* (2013.01);
(Continued)

(58) Field of Classification Search
CPC ............................. C12M 33/06; C12M 33/02
See application file for complete search history.

(56) References Cited

U.S. PATENT DOCUMENTS 5,455,008 A    10/1995 Earley et al.
2002/0090320 A1*  7/2002 Burow ................... B01L 9/523
422/561

(Continued)

FOREIGN PATENT DOCUMENTS

EP    2807484 B1    5/2016
JP    H09187270 A    7/1997
(Continued)

*Primary Examiner* — Nathan A Bowers
(74) *Attorney, Agent, or Firm* — Thomas P. O'Connell; O'Connell Law Firm (57) ABSTRACT A device and a process to count a number of colonies present in a set of samples. The colony counting device has a storage device with plural storage locations. A handling system is operative to convey samples to analyze from storage locations to an analysis area and from the analysis area to storage locations. An imaging device is operative to acquire a plurality of images of a sample to analyze, the plurality of images including all or a part of the analysis area. A processing unit is operative to implement, for each sample to analyze, a detection step to detect the presence of colonies by analyzing an image of the plurality of images of the sample and a determination step to determine the number of colonies present in the sample by counting the colonies whose presence have been detected during the detection step.

7 Claims, 2 Drawing Sheets (51) Int. Cl.
    *G06V 20/69*    (2022.01)
    *C12M 1/34*    (2006.01)
    *C12Q 1/04*    (2006.01)
    *G06T 7/62*    (2017.01)
    *G01N 35/00*    (2006.01)

(52) U.S. Cl.
    CPC ......... *G01N 35/00584* (2013.01); *G06T 7/62* (2017.01); *G06T 2207/30024* (2013.01)

(56) References Cited

U.S. PATENT DOCUMENTS

| | | | |
|---|---|---|---|
| 2003/0040104 A1 | 2/2003 | Barbera-Guillem | |
| 2005/0123445 A1 | 6/2005 | Blecka et al. | |
| 2007/0258858 A1 | 11/2007 | Rasnow et al. | |
| 2012/0258525 A1 | 10/2012 | Izumi et al. | |
| 2013/0109051 A1 | 5/2013 | Li et al. | |
| 2014/0056504 A1* | 2/2014 | Lee | G06T 7/174 382/133 |

FOREIGN PATENT DOCUMENTS

| | | |
|---|---|---|
| JP | H11221070 A | 8/1999 |
| WO | WO9401528 | 1/1994 |

* cited by examiner

PROCESS AND DEVICE FOR COLONY COUNTING

RELATED APPLICATIONS

This application is a divisional application of U.S. patent application Ser. No. 15/877,636, filed Jan. 23, 2018, which claims priority to French Application No. 17 50530, filed Jan. 23, 2017, both incorporated herein by reference to the extent permitted by law.

FIELD OF THE INVENTION

The present invention is in the field of microorganism detecting in a growth medium. More particularly, disclosed herein is a method and device for performing early-counting of bacterial colonies in culture mediums of a group of samples and for automatic management of ongoing sample analysis. The disclosed process and device are notably suitable for microbiological analysis and quality control. The process and device can, for instance, be implemented in the environmental, agri-food, pharmacologic, cosmetic, and research and development fields.

BACKGROUND OF THE INVENTION

Colony counting today is still achieved, in a significant proportion, by manual counting of the colonies visually observed in a plated culture medium. In the prior art, there are colony counting devices based on image acquisition of a sample, which comprises a culture medium previously plated, before processing the images to determine of colonies.

European Patent No. EP2807484 describes a detection device for microorganisms that comprises a sensing system, specifically a scanner, arranged to scan an area with the upper surfaces of a set of plated samples, these samples being positioned side by side on the surface of a platter. The images are then analyzed by image processing software to identify and count the colonies. One drawback of such a device is that each sample to analyze is exposed to lighting during the time needed for the acquisition process. Thus, when counting photosensitive micro-colonies or when using photosensitive markers, this type of device cannot be used.

Another drawback of such a device is that, if the device is not equipped with an optical system to allow adjusting the focal length, it is necessary to use the same culture medium support for all samples. In case the device is equipped with an optical system to adjust focal length, the time required to acquire all samples is significantly increased.

SUMMARY OF THE INVENTION

One purpose of this invention is to offer a device and a process that addresses, at least partly, the various above-mentioned drawbacks.

Another purpose of this invention is to reduce the time needed to count the definitive number of colonies present in a plated culture medium of a sample.

Another purpose of this invention is to reduce the counting error rate.

Another purpose of this invention is to propose a device that allows loading or unloading of samples without interrupting or interfering with the analysis of other samples that are underway.

These and other objects and advantages will be appreciated by one skilled in the art reviewing the present disclosure and to one who has the opportunity to observe an embodiment of the invention in use.

In one practice of the invention, a process for counting a number of colonies present in a set of samples to analyze, each sample of the set of samples to analyze being stored in a storage location of a storage device, each sample of the set of samples to analyze comprising a culture medium support arranged to receive a plated culture medium, the process comprising, for each sample to analyze, a conveyance step of the sample comprising an outward conveyance step from its storage location to an analysis area; a conveyance step of the sample comprising a return conveyance step from the analysis area to a storage location; an acquisition step during which a plurality of images are acquired of all or a part of the analysis area in which the sample is positioned; a detection step to detect a presence of colonies in the sample; and a determination step to determine the number of colonies present in the sample by counting the colonies whose presence has been detected during the detection step. The steps can be performed in a regulated chamber and, potentially, following a predetermined instruction for temperature in the regulated chamber.

As taught herein, the detection step to detect the presence of colonies in the sample and the determination step to determine the number of colonies present in the sample by counting the colonies whose presence has been detected during the detection step can be carried out by a processing unit, such as automatically by the processing unit. As used herein, reference to the processing unit means an electronic processing unit. The processing unit is operative to implement, for each sample to analyze, the detection step to detect the presence of colonies by analyzing an image of the plurality of images of the sample to analyze and the determination step to determine the number of colonies present in the sample to analyze by counting the colonies whose presence have been detected during the detection step.

The outward conveyance step of a sample of the set of samples to analyze can be implemented before the return conveyance step of another sample of the set of samples to analyze. Moreover, the process can include an iteration of all steps, some steps, or each step of the process. In one such practice of the process, for each sample of the set of samples to analyze, an iteration frequency of the acquisition step can be higher than a predetermined frequency. By way of example, the predetermined frequency can be between approximately every 10 minutes and every 120 minutes.

It is further disclosed herein for the detection step to detect the presence of colonies to comprise a step to identify an item on an image of the plurality of images and a second step to analyze for a variation in size of the item identified using one or several other images of the plurality of images. When the size of the item identified varies, an identification of the presence of a colony to detect the presence of a colony. For example, an identification of the presence of a colony can be made when the size of the item identified varies from 51 to 1,000 µm.

The process can additionally include a definitive number step that determines a number of colonies present in the sample comprising a definitive number. The definitive number step can comprise an analysis for a variation in a number of colonies present in the sample determined during the determination step, the determination of a definitive number of colonies being when the number of colonies present in the sample is steady over a period equal to or greater than a predetermined value. In certain practices, once the definitive number step is achieved, the sample is withdrawn from the set of samples to analyze.

It is further contemplated that the process can include the addition of a sample to the set of samples to analyze by loading it in the storage device and, additionally or alternatively, the removal of a sample from the set of samples to analyze by unloading the sample from the storage device. The addition or removal can be performed simultaneously with any other step of the process.

The process can additionally include the step of calculating, such as automatically calculating by the processing unit, a sample acquisition sequence for the set of samples to analyze and a determination of a conveyance sequence, such as by the processing unit, of the set of samples based on the calculated acquisition sequence. Still further, there can be a modification of the set of samples to analyze during which the step of calculating the sample acquisition sequence and the step of the determination of the conveyance sequence are implemented following a modification of the set of samples to analyze. The step of calculating the sample acquisition sequence and the step of the determination of the conveyance sequence can be implemented after each modification of the set of samples to analyze. Some or all of the steps set forth herein can be carried out entirely or partially, selectively or automatically by the processing unit.

A colony counting device according to the invention includes a storage device comprising plural storage locations configured to receive samples to analyze. Each sample comprises a culture medium support configured to receive a plated culture medium. A handling system is operative to convey one or more samples to analyze from one or more storage locations to an analysis area configured to receive one or more samples to analyze and from the analysis area to one or more storage locations. An imaging device is operative to acquire a plurality of images of a sample to analyze, the plurality of images including all or a part of the analysis area, and a processing unit is operative to implement, for each sample to analyze, a detection step to detect the presence of colonies by analyzing an image of the plurality of images of the sample to analyze and a determination step to determine the number of colonies present in the sample to analyze by counting the colonies whose presence have been detected during the detection step.

The processing unit can be further operative to implement, for each sample to analyze, an analysis of a variation in the number of the colonies present in the sample to analyze and determined during the determination step and the determination of a number comprising a definitive number of colonies present in the sample to analyze when the number of colonies present in the sample to analyze is steady over a period of time equal to or greater than a predetermined value. Still further, the processing unit can be further operative to provide a communication to alert an operator when a definitive number of colonies present in the sample to analyze has been determined.

The handing system of the colony counting device can comprise a robotic arm. The robotic arm can have a clamp gripper operative to seize a sample to analyze by clamping. The clamp gripper can incorporate a force sensor operative to limit a maximum clamping force exerted by the clamp gripper when seizing a sample.

Also as taught herein, at least the plural storage locations of the storage device can be mobile. For instance, the storage device can comprise a rotatable carousel. The carousel can have a set of identified storage locations distributed around a central axis of the carousel. The identified storage locations can be disposed in at least one of columns or rows, potentially both in rows and columns.

It is even further contemplated that the processing unit may be operative to calculate an acquisition sequence of the samples to analyze and to calculate a conveyance step of the samples to analyze based on the calculated acquisition sequence. The processing unit may be further operative to calculate the acquisition sequence and the conveyance sequence of the samples to analyze after at least one of the following: an addition of a sample to the set of samples to analyze by loading the sample in the storage device; each removal of a sample from the set of samples to analyze by unloading the sample from the storage device; or each implementation of the determination step.

One will appreciate that the foregoing discussion broadly outlines certain more important goals and features of the invention to enable a better understanding of the detailed description that follows and to instill a better appreciation of the inventor's contribution to the art. Before any particular embodiment or aspect thereof is explained in detail, it must be made clear that the following details of construction and illustrations of inventive concepts are mere examples of the many possible manifestations of the invention. It will thus be clear that additional features and benefits of the invention will be apparent through a reading of the detailed description of implementations and embodiments, which are without restriction, and by reference to the attached figures.

BRIEF DESCRIPTION OF THE DRAWINGS

Additional features and benefits of the invention will be apparent after reading the detailed description of implementations and embodiments of the invention and after review of the accompanying drawings wherein.

DETAILED DESCRIPTION OF PREFERRED EMBODIMENTS

The process and device for colony counting disclosed herein is subject to a wide variety of embodiments. However, to ensure that one skilled in the art will fully understand and, in appropriate cases, be able to practice the present invention, certain preferred embodiments of the broader invention revealed herein are described below and shown in the accompanying drawings. These embodiments are illustrative and are without limitation of the scope of the invention.

In view of the present disclosure, variants of the process or the device may become apparent. Certain variants may include only a selection only of certain disclosed features, each such feature offering a technical benefit or differentiating the invention from the state of the art. Certain selected features may be, or may be interpreted to be, functional without structural limitation or with only such structural limitation as may be sufficient to provide a technical advantage or to differentiate the invention with regard to the prior art. Certain variants and embodiments disclosed herein may be exploited independently or in combination. The protection of the invention shall be limited only by the express terms of the claims.

The disclosed process and device propose to count colonies present in a set of samples to analyze. Each sample of the set to analyze is stored in a location of a storage device. Each sample of the sample set to analyze comprises a culture medium support to receive a plated culture medium. In one practice of the invention, the process comprises, for each sample of the sample set to analyze, the following steps: a conveyance step of the sample, named outward conveyance, from its storage location to an analysis area; a conveyance step of this sample, named return conveyance, from the analysis area to a storage location; an acquisition step during which a number of images of the analysis area, or only of the part of the analysis area where the sample has been positioned, is acquired; a step to detect the presence of colonies in the sample, including an analysis of the set of images of the sample; and a step to determine the number of colonies present in the sample by counting the colonies that were detected during the detection step.

The sum of the process steps according to the invention can be performed in the same chamber regulated according to a predetermined temperature guideline. Each storage location can be referenced. Each sample can have a dedicated location in the storage device. Each sample can be identified by its location reference. The location of a sample stored in the storage device can be determined by its location reference. Samples stored in the storage device may not be analyzed.

The analysis area can mean a volume of space. An image of the whole volume of space that forms the analysis area can be acquired. An image of only a part of the whole volume of space that forms the analysis area can be acquired. An image of the analysis area, or a part of the analysis area, in which a sample is positioned can be acquire regardless of whether the support has a lid or not.

The process of the invention can include image processing by image processing software. The image processing permits a magnification of the image or a part of the image. The image magnification can, for example, be performed before the detection step, during which the presence of colonies in a sample is detected, or before the step during which the number of colonies present in a sample is determined.

Preferably, the magnification can be performed before the detection step during which the presence of colonies in a sample is detected. The image processing software can be any image processing software known by a skilled person in the art. Images of the samples can be acquired, preferably at regular time intervals.

According to the invention and by means of the image acquisition device, a first acquisition of a first image of a sample to analyze that is positioned inside the analysis area can be made consecutively to the sample loading within a maximum time interval. In certain practices, the maximum time interval during which the first image of a sample can be acquired can be between 10 and 120 minutes, preferably from 20 to 60 minutes. The process can comprise a video made from the plurality of images of a sample to analyze.

The culture mediums used for the implementation of the process can be, preferably, solid culture mediums. The culture mediums used for the implementation of the process can notably be agar-based mediums or gelled mediums. When positioned in the analysis area, the sample to analyze can occupy the entire space volume of the analysis area. When positioned in the analysis area, the sample to analyze can occupy only a part of the space volume of the analysis area. When positioned in the analysis area, the sample to analyze may be placed elsewhere than on the surface of the analysis area; in this case, the acquisition is performed while the sample is carried by the handling system.

Preferably, the plurality of images is not acquired during a sole acquisition step but during several subsequent image acquisition steps instead. Preferably, the plurality of images is not acquired during a sole acquisition step but during several subsequent image acquisitions of several space areas instead.

According to the invention, the outward conveyance step of one sample of the set to analyze can be implemented before the return conveyance step of another sample of the set of samples to analyze. Several samples to analyze can be positioned simultaneously, or not, in the analysis area. Several samples to analyze can be deposited in the analysis area. Several samples to analyze can be deposited in the analysis area, and one or several additional samples to analyze can be positioned in the analysis area without being deposited.

According to the invention, the imaging device can image the whole analysis area or a part of it in which is/are positioned one or several sample(s) to analyze in a time frame during which the conveyance system conveys another sample to analyze from the analysis area to the storage device and/or conveys another sample to analyze from the storage device to the analysis area.

According to the invention, the process can comprise an iteration of all steps or an iteration of each step of the process. The number of iterations of one of the step can be different from the number of iterations of another step. The number of iterations of one step can be different from the number of iterations of several other steps. The number of iterations of one of the step can be different from several different numbers of iterations of several other steps. The number of iterations of one of the steps can be different from the number of iterations of all other steps. Each step could, but need not necessarily, have the same number of iterations.

The process steps can be subsequent following one or several preset sequences. A sequence of steps of the process can be subdivided into several step sub-sequences. The steps of the process can be iterated in such way that the outward conveyance step, the return conveyance step and the acquisition step have the same number of iterations while the steps to detect and determine of colonies have the same number of iterations, yet different from the number of iterations of the outward and return conveyance steps.

The steps of the process can be iterated in such way that the outward conveyance step, the return conveyance step and the acquisition step have the same number of iterations while the steps to detect and determine of colonies have a number of iterations so that, for instance, a number of iterations of the detection step is identical to a number of iterations of the detection step, this number being different from a number of iterations of the outward conveyance, return conveyance and acquisition steps, or a number of iterations of the detection step and a number of iterations of the detection step are different, and a number of iterations of the outward conveyance, return conveyance and acquisition steps is equal to the number of iterations of the detection step, or is equal to the number of iterations of the determination step, or is different to the number of iterations of the both detection and determination step.

The process can comprise a sequence of steps of the process. The process can comprise an iteration of a steps sequence of the process. The process can comprise an iteration of several different sequences of steps of the process.

Preferably, the colony counting process may comprise several iterations of the outward conveyance step and several iterations of the return conveyance step. One or several steps of the same step sequence may be iterated during the same sequence of steps. Each step of a same step sequence can be iterated during the same sequence of steps.

A number of iterations of a step, that is part of a sequence of steps, can be different from another number of iterations of another step of this sequence of steps. A number of iterations of a step, that is part of a sequence of steps, can be different from several other number of iterations of several other steps of this sequence of steps. The number of iterations of the steps among a sequence of steps can be the same.

A number of iterations of a step among a sequence of steps can be different from a number of iterations of the step among another sequence of steps. A sequence of steps implemented for one of the sample to analyze can be different from a sequence of steps implemented for another sample to analyze.

According to the invention, the detection step to detect the presence of colonies can comprise a first step to identify an item on an image of the plurality of images, a second step to analyze a variation in size of the identified item on one or several images of the plurality of images, and an identification of the presence of a colony if the size of the item vary.

The step that identifies the item on an image can be performed by any image analysis technique that would be known to a person skilled in the art made aware of this disclosure. The step of analyzing the variation in size of an item identified on one or several images can be performed by any image analysis technique that would be known to a person skilled in the art made aware of this disclosure.

The analysis of a variation in the size of an item identified on one or several images can be a function of time. The analysis of a variation in size of an item identified on one or several images can be a function of any time-related variant, such as a number of iterations of one or several steps or the number of iterations of one or several sequences for instance. Preferably, the analysis of a variation in size of an item identified on one or several images can be performed after each acquisition step.

The variation in size of an identified item can be determined from two sequential images of a sample to analyze. The variation in size of an identified item can be determined from two non-sequential images of a sample to analyze. The variation in size of an identified item can be determined from several sequential images of a sample to analyze. The variation in size of an identified item can be determined from several non-sequential images of a sample to analyze.

Advantageously, the step that detects the presence of colonies can comprise a first step to identify the item on an image of the plurality of images; a second step to analyze the variation in size of the item identified on one or several other images of the plurality of images; and an identification of the presence of a colony when the size of the item vary of a value comprised between 51 and 1 000 µm, preferably between 100 and 200 µm. The minimal size of a detected colony can be 51 µm.

The process can comprise a step to determine the number of colonies present in the sample, referenced as "definitive", this step comprising an analysis of a variation in the number of colonies present in the sample that was determined during the determination step and the determination of the definitive number of colonies when the number of colonies is steady over a time period longer than a predetermined time value.

The analysis of a variation in number of the colonies, determined during the determination step, can be a function of time. The analysis of a variation in number of the colonies, determined during the determination step, can be a function of any time-related variant, such as a number of iterations of one or several steps or the number of iterations of one or several sequences for instance. Preferably, the analysis of a variation in number of the colonies, determined during the determination step, can be implemented after each determination step.

The predetermined time value during which the number of colonies that has been determined during the step that determines the number of colonies in a sample can, for example, be between 6 and 72 hours, preferably 8 and 48 hours. The determination of the definitive number of colonies can be a function of time. The determination of the definitive number of colonies can be a function of any time-related variant such as a number of iterations of one or several steps or the number of iterations of one or several sequences for instance. Preferably, the determination of the definitive number of colonies can be determined when the number of colonies determined during the step that determines the number of colonies in the sample is constant during at least two iterations of the step, preferably four iterations.

The predetermined value of the duration during which the number of colonies must be constant so that it may be considered definitive can additionally be determined according to the culture medium contained in the sample support. The predetermined value of the duration during which the number of colonies must be constant so that it may be considered definitive can additionally be determined according to a bacterial strain.

Any time-related variable such as a number of iterations of one or several step or a number of iterations of one or several sequences, for instance, can be substituted by the duration during which the number of colonies must be constant so that the definitive attribute can be attributed to the number of colonies. According to the invention, once the step that determines the definitive number of colonies is achieved, the sample can be withdrawn from the set of samples to analyze.

Following the determination of the definitive number of colonies in the sample to analyze, the sample may not be considered as a sample to analyze, but may remain stored in the storage device. The determination of the definitive number of colonies present in the sample to analysis may coincide with the end of the process implementation for this sample. If, after a predetermined duration, no item has been identified on any image of the plurality of images of a sample during the detection step that determined the presence of colonies, the definitive number of colonies present in the sample is considered as null.

Advantageously, the process can comprise the addition of a sample to the set of samples to analyze by loading this sample in the storage device, and, additionally or alternatively, the removal of a sample to the set of samples to analyze by unloading this sample from the storage device. The addition and, additionally or alternatively, the removal can be performed simultaneously with any step of the process. Additionally, the loading and, additionally or alternatively, the unloading of a sample in the device can be performed by an operator. Loading and unloading can be performed simultaneously.

When loading a sample in a location of the storage device, the processing unit can be configured so that the storage device brings an empty location before the operator. When unloading a sample from a location of the storage device, the processing unit can be configured so that the storage device brings before the operator the location in which this sample is stored.

When loading and/or unloading a sample and a step is being implemented at the same time, the processing unit can put the step on hold while the loading or the unloading is being performed. When loading and/or unloading a sample, the processing unit can be configured so that it sets aside the storage device handling system, and/or immobilizes the handling system.

The process can comprise a calculation step to calculate a sample acquisition sequence for the set of samples to analyze, and the determination of a conveyance sequence for this set as of the calculated acquisition sequence. For each sample to analyze, a sequence of steps of the process to apply to this sample can be calculated by the processing unit, depending on the acquisition sequence of the samples to analyze.

The conveyance sequence is determined by the processing unit so that it follows the acquisition sequence. An analysis sequence of a sample can be defined as the total number of steps applied to the sample, from a first outward conveyance step to a final return conveyance step. Following the last return conveyance step of a sample and following the determination step that determines the definitive number of colonies present in the sample, the analysis sequence of the sample can be completed.

According to the invention, the process may comprise the modification of the entire set of samples to analyze, the calculation steps of the acquisition sequence and the determination of the conveyance step being implemented after the modification of the set of samples to analyze. By modification of the set of samples, we can mean for instance: loading one or several samples, or unloading one or several samples, or determining the definitive number of colonies present in the sample to analyze.

Advantageously, the calculation step of the acquisition sequence and the determination step of the conveyance sequence can be implemented following each modification of the set of samples to analyze. Any number of iterations of one or several steps of the process can be redefined by a processing unit during the implementation of the process. One or several sequences of steps can be redefined by a processing unit during the implementation of the process. Any number of iterations of one or several sequences of steps can be redefined by a processing unit during the implementation of the process. For each sample to analyze, the process steps can be iterated following one or several sequences redefined by a processing unit during the implementation of the process.

According to the embodiments of the invention, for each sample of the set of samples to analyze, an iteration frequency of the acquisition step can be higher than a predetermined frequency, this predetermined frequency preferably comprises between every 10 minutes to every 120 minutes. The iteration frequency of the acquisition step of a sample to analyze may be different from the iteration frequency of another sample to analyze. The iteration frequency of the acquisition step of a sample to analyze may vary depending on a time factor. Preferably, the iteration frequency of the acquisition step of a sample can increase when the variation of the number of colonies present in the sample, determined during the determination step decreases after having increased.

A maximal conveyance speed of the conveyance device may require the redefinition of the conveyance sequence of the set of samples so that the minimal iteration frequency of the sample acquisition set is respected. For instance, one or several samples may be deposited in the area so that it removes the return conveyance step from a sequence or a sub-sequence of steps applied to the sample(s).

According to another aspect of the invention, a colony counting device is proposed and it comprises: a storage device comprising locations arranged to receive samples, these samples comprising a culture medium support arranged to receive a plated culture medium, a handling system arranged to convey one or several samples to analyze from one or several locations to an analysis area and from this analysis area to one or several locations, and an imaging device configured so that, for each sample to analyze, it implements: a detection step to detect the presence of colonies by the analysis of images among a plurality of images of a sample to analyze and a determination step that determines, by counting the colonies whose presence was detected during the detection step, the number of colonies present in the sample to analyze.

Advantageously, the device may comprise a closed chamber in which the storage device, the handling system, and the imaging device are arranged. Advantageously, the closed room may be an incubator allowing: temperature control, and/or hygrometry control, and/or $CO_2$ control. As taught herein, the device can further include a device to light the analysis area.

The support can be a box. The support can be a box with a lid. The support may be any type of support that might be known by a skilled person being made aware of this disclosure, including a Petri dish.

The culture medium may be any type of medium fit for the multiplication of one or several specific microorganisms. The culture medium may be any type of medium fit for the multiplication of one or several ordinary microorganisms. The culture medium may be any type of medium, crafted or industrial, known by the skilled person in the art.

Preferably, each location can preferably be arranged to receive only one sample at a time. Several locations can preferably referenced. The handling system can be arranged to convey several samples subsequently. The handling system can be arranged to convey several samples simultaneously. The storage device can be mobile. The storage device can be set in motion with respect to the handling system.

The imaging device can comprise an optical device. All or part of the imaging device can be mobile. The imaging device can perform 32-fold magnification. The imaging device can comprise an optical device arranged to perform the magnification of all or part of the analysis area such as a lens for instance. The imaging device can be able to image the entire volume of space that constitutes the analysis area, by means of several acquisitions. The imaging device can be arranged to independently image several parts of the analysis area. The resolution of a digital image acquired by the imaging device can be comprised, without limitation, between 500×500 pixels and 3,000×3,000 pixels.

The imaging device can comprise any type of photosensitive calculator that might be known by a skilled person in the art in view the present disclosure. According to the invention, the processing unit may additionally be configured to implement, for each sample to analyze, an analysis of the variation in number of the colonies present in the sample to analyze and determined during the determination step and when the number of colonies is constant over a time period higher than a predetermined value, a number of colonies present in the sample to analyze and called definitive, is determined.

The device may include an alarm and/or communication system to alert and/or communicate, that is arranged to warn the operator of the determination of the definitive number of colonies present in a sample and/or a set of samples. The alarm and/or communication means is arranged to warn and/or notify the operator that the sample and/or the set of samples is in a condition ready to be unloaded from the storage device. The alarm means can be any technical mechanism capable of emitting a signal that would be known to a person of skill in the art in view of the present disclosure. Similarly, the alarm and/or communication system may be able to emit, additionally, a visible or audible signal. The communication means may be any technical means able to transmit a signal and known of the skilled person in the art. The communication means may additionally be able to transmit an electronic message and/or a text message and/or a phone call.

The handling system may comprise a robotic arm. The arm can be a clamp gripper arranged to seize a sample to analyze by means of gripping. The robotic arm may be articulated around a central component. The robotic arm may rotate around a pivot. The clamp gripper may be mobile along the robotic arm. The handling system may comprise several robotic arms.

In certain embodiments, the storage device takes the form of a carousel. The carousel has a set of referenced storage locations arranged around a central axis of the carousel, preferably in the shape of columns and/or rows. The samples can, for example, be referenced by entering their references in a processing unit. The sample can be identified by the referenced location in which it is stored. The sample can be localized by the referenced location in which it is stored. As used herein, a carousel can be defined to include a central axis around which a set of storage locations is arranged. Each storage location may alternatively be referred to herein as a storage location.

A storage location can be set in motion with respect to the central axis and another location. A location can be set in motion with respect to the central axis and several other locations. A location can be set in motion with respect to the central axis and all the other locations. Several storage locations can be set in motion with respect to the central axis of the carousel. All locations can be set in motion jointly with respect to the central axis of the carousel. Storage locations can be set in a rotary motion around the central axis of the carousel. All locations can be set in a rotary motion jointly around the central axis of the carousel.

According to the invention, the processing unit may additionally be arranged to calculate an acquisition sequence of the samples to analyze. The processing unit can also calculate a conveyance sequence of the samples to analyze the calculated acquisition sequence. Preferably, the storage device can have a maximal number of locations adapted to the conveyance speed of the handling system so that the minimal analyze frequency of a sample is higher than 2 analyses per hour.

The processing unit can additionally be configured to calculate the sample's acquisition and conveyance steps following: each addition of a sample to the set of samples to analyze by loading this sample into the storage device, and/or each withdrawal of a sample from the set of samples to analyze by unloading this sample from the storage device, and/or each implementation of the determination step to determine the number of colonies present in one of the samples to analyze.

According to the invention, the clamp gripper can include a force sensor arranged to limit the maximal effort exerted by the clamp gripper when seizing a sample so that the clamp gripper is able to seize a sample, such as a Petri dish whose size is comprised between 50 and 100 mm diameter, by gripping any part of it. Advantageously, the clamp gripper may be arranged to seize a sample by its lateral edges. The clamp gripper can be arranged to seize a sample by lateral edges located on the sides of the location surface on which the sample has been placed. The clamp gripper can be arranged to seize a sample by lateral edges located at close proximity of the location surface sides on which the sample has been placed.

The carousel may comprise storage towers, the storage towers comprising superimposed locations and being located around the central axis of the carousel. Storage towers may be set in motion with respect to the central axis of the carousel. The storage towers may be set in motion jointly with respect to the central axis of the carousel. Storage towers may be set in rotary motion around the central axis of the carousel. The storage tower may be set in rotary motion jointly around the central axis of the carousel. The carousel may comprise storage containers, these containers comprising juxtaposed locations and being located around the central axis of the carousel. The carousel may comprise rails, these rails being arranged so that the storage towers and/or the storage containers may slide into the rails when set in motion.

The embodiments described herein after are not limiting. One can notably imagine variants of the invention that would include only a selection of the features described isolated from the others described features even if this selection is isolated in a phrase that comprises these other features for this selection of features is proved as offering a technical benefit or to differentiate the invention in regard of the state of the art. This selection comprises at least one preferable functional feature without structural specificities, or with only a part of structural details if this sole part is enough to provide a technical advantage or to differentiate the invention with regard to the prior art.

Figure 1:
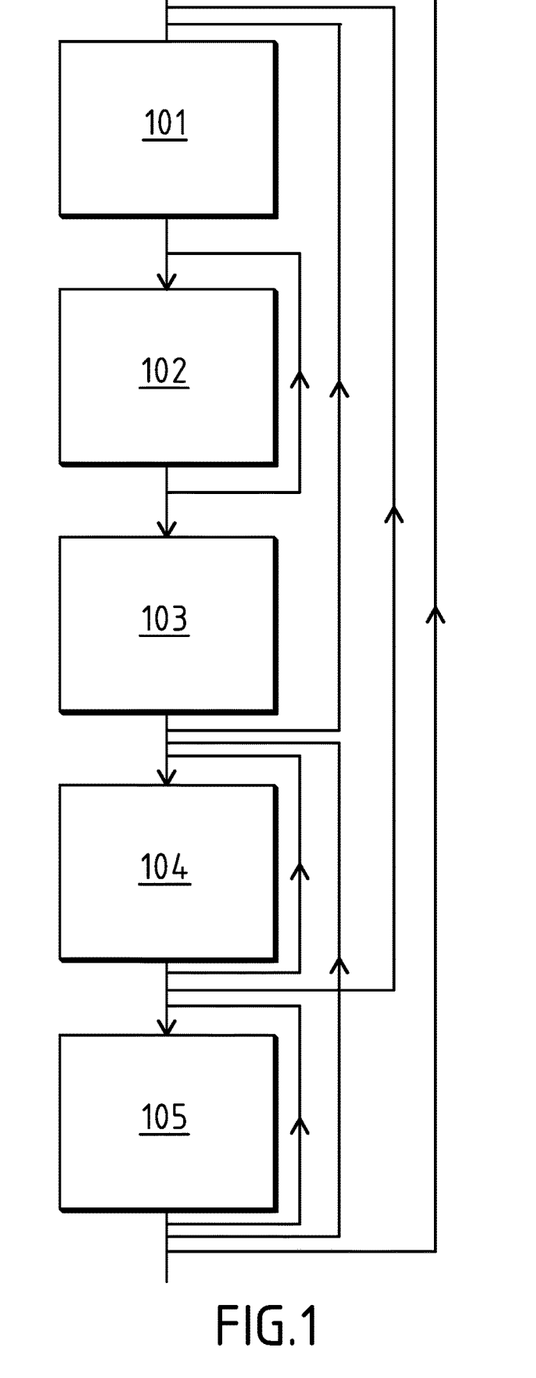
FIG. 1 is a diagram illustrating a sequence of steps in the counting process of different colonies.
Figure 3:
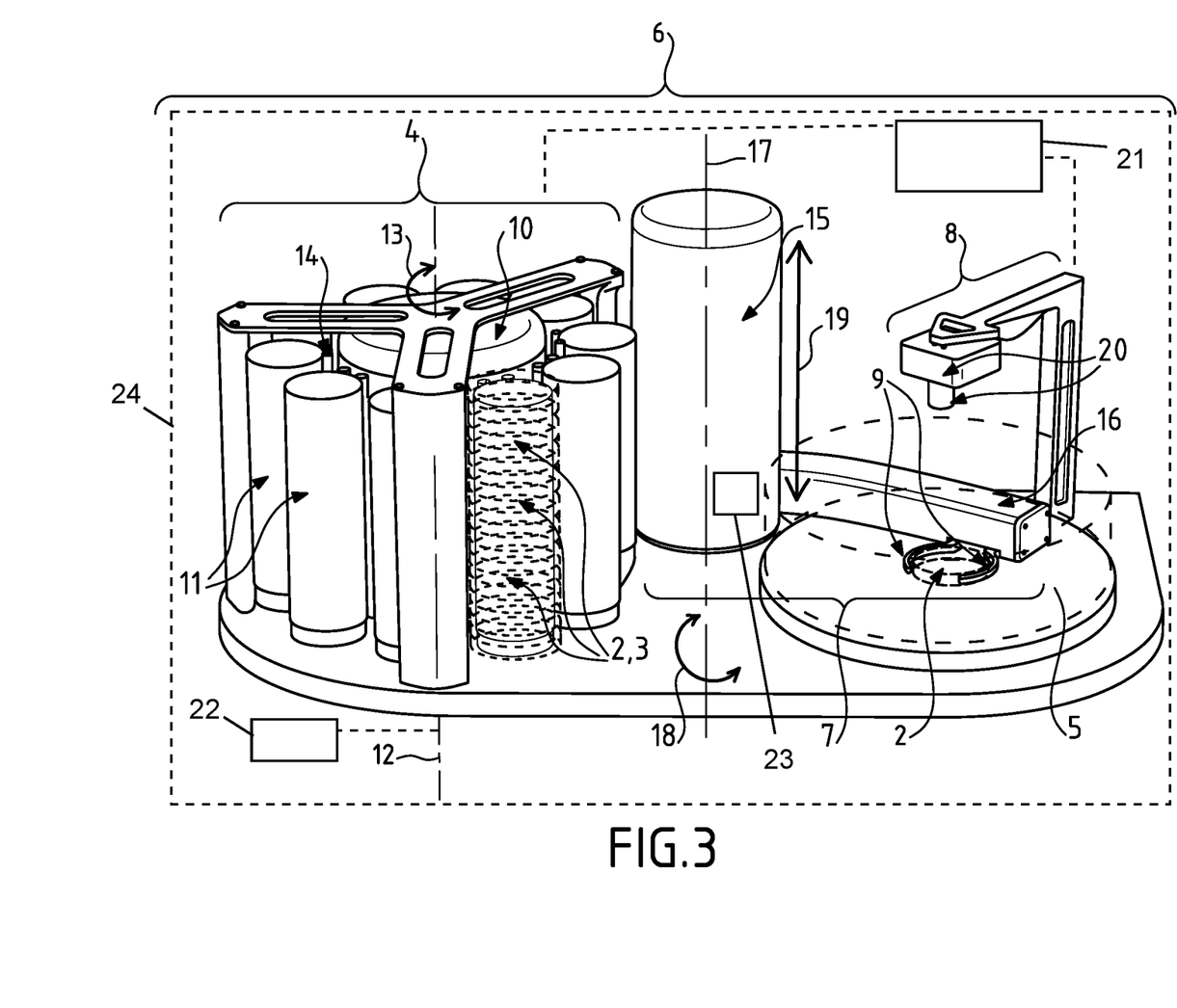
FIG. 3 is a schematic view of a colony counting device according to the invention.

In reference to FIGS. 1 and 3, a first embodiment of the process of the invention is depicted, the process comprising counting colonies present in a set of samples to analyze. Each sample 2 of this set of samples to analyze can be stored in a location 3 of a storage device 4. Each sample 2 of the set of samples to analyze comprises a culture medium support arranged to receive a plated culture medium. In certain practices, this process comprises, for each sample 2 of the set of samples to analyze, the following steps, which may but need not be done in order except as expressly required by the claims: a conveyance step of the sample 2, which may be referred to as an outward conveyance 101, from its location 3 to an analysis area 5; an acquisition step 102 during which is acquired a plurality of images of the analysis area 5 or a part of the analysis area 5 in which the sample 2 is positioned; a conveyance step 102 of the sample 2, which may be referred to as a return conveyance, from the analysis area 5 to a location 3; a detection step 104 to detect the presence of colonies in the sample 2 and comprising image analysis from the plurality of images of the sample 2, a determination step 105 to determine the number of colonies present in the sample 2 by counting the colonies whose presence had been detected during the detection step 104.

Two or more images of a sample 2 can be acquired, the acquisition of the images being spaced by a time period. For example, the time between the acquisitions of two subsequent images of a sample 2 to analyze can be less than 30 minutes. This minimal acquisition frequency is reached when all locations 3 of the storage location 4 are filled with samples 2 to analyze. The acquisition frequency increases when the number of samples 2 to analyze stored in the storage device 5 decreases. According to one contemplated embodiment, one sample 2 is disposed in the analysis area 5 at a given time. Under such constructions, several samples 2 would not be simultaneously present in the analysis area 5.

In one iteration of the sequence of steps identical to the one depicted in FIG. 1, the outward conveyance 101 and the return conveyance 103 steps have the same number of iterations.

The outward conveyance 101 and the return conveyance 103 steps, if the iteration sequence is as depicted on FIG. 1, have the same number of iterations. Each of the steps 102, 104, and 105 are iterated following an iteration of the sequence of steps as depicted in FIG. 1, independently of the other steps.

Following a second embodiment of the process, according to the invention, described for its differences with the first embodiment, the detection step 104 and the determination step 105 form a first sub-sequence 104,105 iterated following an iteration of the sequence of steps as depicted in FIG. 1, independently of the other steps. In an iteration of the sequence of steps identical as the one depicted in FIG. 1, the outward conveyance 101 and the return conveyance 103 steps have the same number of iterations. The acquisition step 102 is iterated following an iteration of the sequence of steps as depicted in FIG. 1, independently of the other steps and the first sub-sequence. The number of iterations of the acquisition step 102 can be: identical to the number of iterations of steps 101 and 103, and identical to the number of iterations of the first sub-sequence 104,105, or identical to the number of iterations of steps 101 and 103, and different from the number of iterations of the first sub-sequence 104,105, or different from the number of iterations of steps 101 and 103, and identical to the number of iterations of the first sub-sequence 104,105, or different from the number of iterations of steps 101 and 103, and different from the number of iterations of the first sub-sequence 104,105.

Following a third embodiment of the process according to the invention, described for its differences with the first embodiment, the steps 101, 102, and 103 form a second sub-sequence 101,102,103 iterated following an iteration of the sequence of steps as depicted in FIG. 1, independently of the first sub-sequence 104,105. The number of iterations of the first sub-sequence 104,105 is, in this example, different from the number of iterations of the second sub-sequence 101, 102, and 103.

Following a fourth embodiment of the process, according to the invention, the sequence of steps as displayed in FIG. 1 is fully iterated, each step of the sequence, if iterated the same way than the sequence of steps, having an identical number of iterations.

Figure 2:
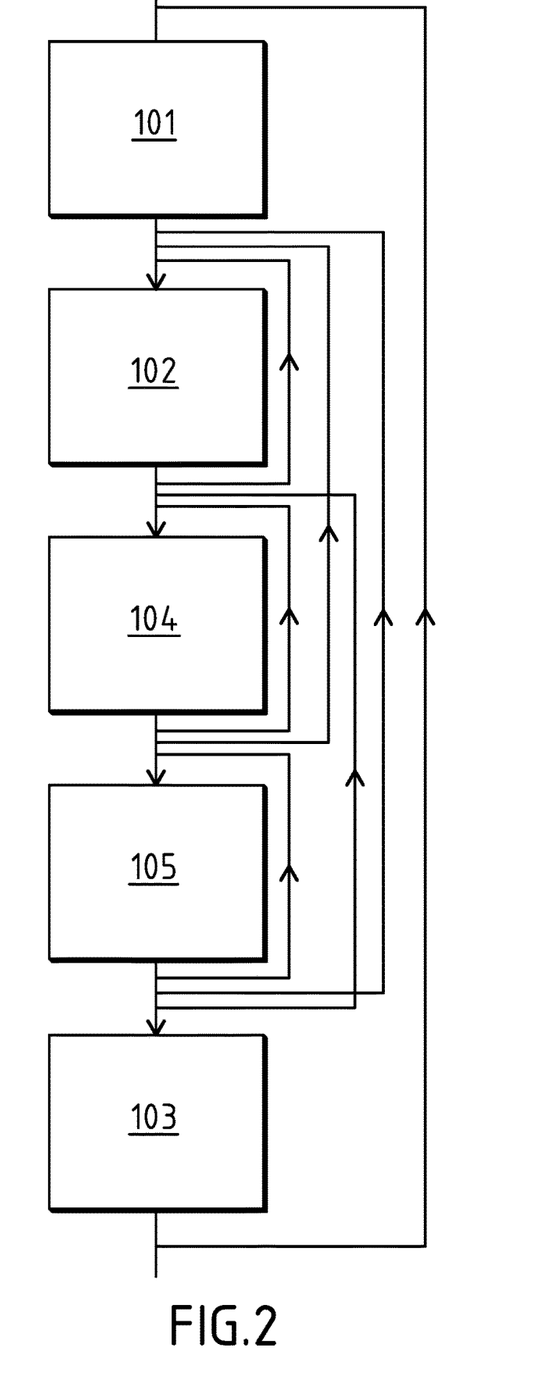
FIG. 2 is a diagram illustrating another sequence of steps in the counting process of different colonies.

In reference to FIGS. 2 and 3, a sequence of steps of the colony counting process according to this invention is shown and described following a fifth embodiment of the process according to the invention described for its differences with the first embodiment. For each sample 2 to analyze, the process is implemented following the sequence of steps hereinafter: step 101, then step 102, then step 104, then step 105, then step 103.

The outward conveyance 101 and the return conveyance 103 steps, iterated following an iteration of the sequence of steps as depicted in FIG. 2, have the same number of iterations. Each of the steps 102, 104, and 105 is iterated following an iteration of the sequence of steps as depicted in FIG. 2, independently of the other steps.

Following a sixth embodiment of the process according to the invention, described for its differences with the first embodiment, the steps 102 and 104 form a first iterated sub-sequence 102,104, following an iteration of the sequence of steps as depicted in FIG. 2, independently of the other steps of this sequence of steps. The steps 101 and 103, having their sequence of steps iterated as depicted in FIG. 2, have the same number of iterations. The number of iterations of the step 105 can be: different from the number of iterations of steps 101 and 103, and different from the number of iterations of the first sub-sequence 102,104, or different from the number of iterations of steps 101 and 103, and identical to the number of iterations of the first sub-sequence 102,104, or identical to the number of iterations of steps 101 and 103, and different from the number of iterations of the first sub-sequence 102,104, or identical to the number of iterations of steps 101 and 103, and identical to the number of iterations of the first sub-sequence 102,104.

Following a seventh embodiment of the process according to the invention, described for its differences with the first embodiment, the steps 104 and 105 form a second sub-sequence 104,105 iterated following an iteration of the sequence of steps as depicted in FIG. 2, independently of the other steps of this sequence of steps. The steps 101 and 103, having their sequence of steps iterated as depicted in FIG. 2, have the same number of iterations. The number of iteration of the step 102 can be: different from the number of iterations of steps 101 and 103, and different from the number of iterations of the first sub-sequence 104,105, or different from the number of iterations of steps 101 and 103, and identical to the number of iterations of the first sub-sequence 104,105, or identical to the number of iterations of steps 101 and 103, and different from the number of iterations of the first sub-sequence 104,105, or identical to the number of iterations of steps 101 and 103, and identical to the number of iterations of the first sub-sequence 104,105.

Following an eighth embodiment of the process according to the invention, described for its differences with the first embodiment, the steps 102, 104, and 105 form a third sub-sequence 102, 104, 105 iterated following an iteration of the sequence of steps as depicted in FIG. 2, independently of the steps 101 and 103 that, having their sequence of steps iterated as depicted in FIG. 2, have the same number of iterations. When iterating the sequence of steps as depicted in FIG. 2, the number of iterations of the third sub-sequence is different from the number of iterations of steps 101 and 103.

Following a ninth embodiment of the process according to the invention, described for its difference with the first embodiment, the sequence of steps as displayed in FIG. 2 is fully iterated, each step of the sequence having the same number of iterations for their sequence of steps is iterated as displayed on FIG. 2.

In reference to FIG. 3, an embodiment of the colony counting device 6 according to the invention is proposed, this device 6 comprising: a storage device 4 comprising locations 3, which may be referred to as storage locations 3, arranged to receive samples 2 to analyze, these samples 2 comprising a culture medium support arranged to receive a plated culture medium; a handling system 7 arranged to convey one or several samples 2 to analyze from one or several storage locations 3 to an analysis area 5, and from the analysis area 5 to one or several storage locations 3; an imaging device 8 arranged to acquire a plurality of images of all or part of the analysis area 5, the latter being arranged to received one or several samples 2 to analyze; a processing unit 21 configured to implement, for each sample 2 to analyze: a detection step to detect the presence of colonies by analyzing images from the plurality of images of a sample 2 to analyze, a determination step to determine the number of colonies present in the sample 2 to analyze, by counting the colonies whose presence has been detected during the detection step.

The storage device 4 comprises a carousel with a set of storage towers 11 connected to a central element 10 comprising a revolution axis 12 around which the central element 10 is rotatable in a rotary motion 13 by means of an actuator, schematically indicated at 22. Connection elements 14 connect the storage towers 11 to the central element 10 so that the connection elements 14 set in rotary motion the storage towers 11 when the central element 10 is set in rotary motion. Each storage tower 11 has plural superimposed locations 3, such as ten superimposed locations 3. The storage device 4 has plural storage towers 11, such as ten storage towers 11, positioned at equal distances from the central axis 10 and angularly distributed around the revolution axis 12.

The handling system 7 comprises a pivot structure 15 to which a robotic arm 16 is connected. The pivot structure 15 has a revolution axis 17 around which the pivot structure 15 can be set in rotary movement 18. The rotary movement 18 of the pivot structure 15 is directly transferred to the robotic arm 16. The robotic arm 16 can be moved in vertical translating movement 19 with respect to the pivot 15 by an actuator, schematically depicted at 23.

A clamp gripper 9 is located near the distal end of the robotic arm 16, with respect to the pivot 15. The clamp gripper 9 is equipped with two arms movable in a translating movement with respect to each other in opposite directions. The arms are set in translating movement in a symmetrical and coordinate manner. The translating movement of the arms brings the arms close to each other to clamp a sample 2 or to set the arms apart to release a sample 2. Each arm has a rounded shape optimized to seize round-shaped culture medium supports and notably Petri dishes. In certain embodiments, the maximum distance between each arm can be 15 cm. The clamp gripper 9 comprises a force sensor arranged to limit the clamping force exerted on the sample 2 by the arms when they seize it. The force exerted by the arms can be limited, such as to 5 Newton. The force sensor allows the clamp gripper 9 to seize any round-shaped item measuring less than 10 cm. The clamp gripper 9 can potentially be according to the system and device disclosed in application Ser. No. 15/876,857, filed Jan. 22, 2018, now U.S. Pat. No. 10,434,662, issued Oct. 8, 2019, which is incorporated herein by reference, and in French Application No. 1750528, filed Jan. 23, 2017, which is also incorporated herein by reference to the extent permitted by law.

The imaging device 8 can be maintained in a stationary manner. The imaging device 8 can, in one example, comprise a camera 20, such as a 5 megapixel CCD camera 20.

In one non-limiting embodiment, the analysis area 5 is 10 cm wide and 10 cm long, the camera 20 is located about 25 cm away from the sample 2 to analyze.

The device may include a closed room or chamber, schematically indicated at 24, in which the storage device 4, the handling system 7, and the imaging device 8 are arranged. Advantageously, the closed room 24 may be an incubator allowing: temperature control, and/or hygrometry control, and/or CO2 control. As taught herein, the device can further include a device to light the analysis area.

Of course, the invention is not limited to the examples described herein before, and a number of arrangements can be implemented in these examples without going beyond the framework of the invention. Furthermore, the various characteristics, shapes, variants, and embodiments of the invention can be combined together in various combinations for they are not incompatible or exclusive to each other.

Accordingly, with certain details and embodiments of the present invention for a process and device for colony counting disclosed, it will be appreciated by one skilled in the art that numerous changes and additions could be made thereto without deviating from the spirit or scope of the invention. This is particularly true when one bears in mind that the presently preferred embodiments merely exemplify the broader invention revealed herein. Accordingly, it will be clear that those with major features of the invention in mind could craft embodiments that incorporate those major features while not incorporating all of the features included in the preferred embodiments.

Therefore, the following claims shall define the scope of protection to be afforded to the patent holder. Those claims shall be deemed to include equivalent constructions insofar as they do not depart from the spirit and scope of the invention. Certain claims may express, or be interpreted to express, certain elements as means for performing a specific function, at times without the recital of structure or material. As the law demands, any such claims shall be construed to cover not only the corresponding structure and material expressly described in this specification but also all legally-cognizable equivalents thereof.

What is claimed is:

1. A process to count a number of colonies present in a set of samples to analyze, each sample of the set of samples to analyze being stored in a storage location of a storage device, each sample of the set of samples to analyze comprising a culture medium support arranged to receive a plated culture medium, the process comprising, for each sample to analyze:
   a conveyance step of the sample comprising an outward conveyance step from the storage location of the sample to an analysis area;
   a conveyance step of the sample comprising a return conveyance step from the analysis area to a storage location;
   an acquisition step during which a plurality of images are acquired of all or a part of the analysis area in which the sample is positioned;
   a detection step to detect a presence of colonies in the sample;
   a determination step to determine the number of colonies present in the sample by counting the colonies whose presence has been detected during the detection step;
   providing a colony counting device, the colony counting device comprising:
      a storage device comprising plural storage locations configured to receive samples to analyze, each sample comprising a culture medium support configured to receive a plated culture medium;
      a handling system operative to convey one or more samples to analyze from one or more storage locations of the storage device to an analysis area configured to receive one or more samples to analyze and from the analysis area to one or more storage locations of the storage device;
      an imaging device operative to acquire a plurality of images of a sample to analyze, the plurality of images including all or a part of the analysis area;

a closed chamber comprising an incubator, wherein the storage device with the rotatable carousel, the handling system, and the imaging device are disposed in the incubator; and     a processing unit operative to implement, for each sample to analyze, calculation of an acquisition sequence and a conveyance step based on the calculated acquisition sequence, a detection step to detect the presence of colonies by analyzing an image of the plurality of images of the sample to analyze, and a determination step to determine the number of colonies present in the sample to analyze by counting the colonies whose presence have been detected during the detection step;

wherein the processing unit is further operative to implement, for each sample to analyze, an analysis of a variation in the number of the colonies present in the sample to analyze and determined during the determination step and the determination of a definitive number of colonies present in the sample to analyze, the definitive number of colonies being determined when the number of colonies present in the sample to analyze is steady over a period of time equal to or greater than a predetermined value and wherein the processing unit is further operative to provide an alert communication to an operator when the definitive number of colonies present in the sample to analyze has been determined.

2. The process of claim 1, wherein the determination step includes determining by the processing unit based on counting the colonies whose presence have been detected during the detection step when the number of colonies present in the sample to analyze is steady over the period of time equal to or greater than the predetermined value and the determination by the processing unit of when the definitive number of colonies is present in the sample to analyze, the definitive number of colonies being determined when the number of colonies present in the sample to analyze is steady over the period of time equal to or greater than the predetermined value.

3. The process of claim 2, further comprising the step of providing the alert communication by the processing unit when the definitive number of colonies present in the sample to analyze has been determined.

4. The process of claim 1, wherein the storage device comprises a rotatable carousel with a central element and a plurality of storage towers connected to the central element, wherein each storage tower has plural storage locations, wherein the central element is rotatable in rotary motion by an actuator, and wherein the plural storage towers are set in rotary motion by rotary motion of the central element whereby the plural storage locations are mobile.

5. The process of claim 1, wherein the handling system comprises a robotic arm, the robotic arm comprising a clamp gripper operative to seize a sample to analyze by clamping and a force sensor operative to limit a maximum clamping force exerted by the clamp gripper when seizing a sample and wherein the clamp gripper comprises first and second gripping arms movable with respect to one another with a first position where the first and second gripping arms are in proximity, the first position comprising a clamping position, and a second position where the first and second gripping arms are moved apart with respect to the first position, the second position comprising a slack position, and a drive mechanism that drives the first and second gripping arms with respect to one another at least from the slack position to the clamping position.

6. The process of claim 1, wherein at least the conveyance steps, the acquisition step, and the detection step are performed in the closed chamber comprising the incubator.

7. The process of claim 6, wherein the incubator allows temperature control, hygrometry control, and/or $CO_2$ control.

\* \* \* \* \*